United States Patent
Chang et al.

(10) Patent No.: US 10,762,986 B1
(45) Date of Patent: Sep. 1, 2020

(54) VITAL-SIGN DETECTING SYSTEM AND METHOD

(71) Applicant: Wistron Corporation, New Taipei (TW)

(72) Inventors: Yao-Tsung Chang, New Taipei (TW); Yin-Yu Chen, New Taipei (TW); Chuan-Yen Kao, New Taipei (TW); Sheng-Lun Chiou, New Taipei (TW); Yao-Shun Tseng, New Taipei (TW)

(73) Assignee: Wistron Corporation, New Taipei (TW)

( * ) Notice: Subject to any disclaimer, the term of this patent is extended or adjusted under 35 U.S.C. 154(b) by 0 days.

(21) Appl. No.: 16/408,325

(22) Filed: May 9, 2019

(30) Foreign Application Priority Data

Mar. 5, 2019 (TW) ............................. 108107258 A
Mar. 5, 2019 (TW) ............................. 108107259 A

(51) Int. Cl.
| | |
|---|---|
| G08B 21/00 | (2006.01) |
| G16H 10/65 | (2018.01) |
| A61B 5/0402 | (2006.01) |
| A61B 5/00 | (2006.01) |
| A61B 5/0205 | (2006.01) |
| A61B 90/90 | (2016.01) |
| A61B 5/01 | (2006.01) |
| A61B 5/024 | (2006.01) |
| A61B 5/08 | (2006.01) |

(52) U.S. Cl.
CPC ........... *G16H 10/65* (2018.01); *A61B 5/0015* (2013.01); *A61B 5/02055* (2013.01); *A61B 5/0402* (2013.01); *A61B 90/90* (2016.02); *A61B 5/0008* (2013.01); *A61B 5/01* (2013.01); *A61B 5/024* (2013.01); *A61B 5/0816* (2013.01); *A61B 2562/08* (2013.01)

(58) Field of Classification Search
None
See application file for complete search history.

(56) References Cited

U.S. PATENT DOCUMENTS

| | | |
|---|---|---|
| 2012/0022348 A1 | 1/2012 | Droitcour et al. |
| 2012/0268308 A1 | 10/2012 | Tuttle |

FOREIGN PATENT DOCUMENTS

| | | |
|---|---|---|
| CN | 101472835 A | 7/2009 |
| TW | I511701 B | 12/2015 |
| WO | WO 2001/050407 A1 | 7/2001 |

(Continued)

OTHER PUBLICATIONS

Extended European Search Report dated Jan. 2, 2020 in related European Application No. 19178096.4.

(Continued)

*Primary Examiner* — Adolf Dsouza
(74) *Attorney, Agent, or Firm* — Donald E. Stout; Stout, Uxa & Buyan, LLP

(57) ABSTRACT

A vital-sign detecting system includes radio-frequency (RF) tags disposed on detected subjects respectively, the RF tags respectively generating incident RF signals with different predetermined frequencies, and the incident RF signal projecting on a corresponding detected subject to generate a corresponding reflected RF signal; and at least one RF radar that demodulates the reflected RF signal to obtain vital sign of the corresponding detected subject, and identifies the detected subject according to associated frequency of the reflected RF signal.

8 Claims, 10 Drawing Sheets

(56) References Cited

FOREIGN PATENT DOCUMENTS

WO     WO 2018/232414 A1     12/2018

OTHER PUBLICATIONS

Extended European Search Report dated Jan. 2, 2020 in related European Application No. 19178103.8.
Aditya Singh et al., "Respiratory Monitoring and Clutter Rejection Using a CW Doppler Radar with Passive RF Tags," IEEE Sensors Journal, vol. 12, No. 3, Mar. 2012, pp. 558-565.
Changzhi Li, et al., "A Review on Recent Advances in Doppler Radar Sensors for Noncontact Healthcare Monitoring," IEEE Transactinos on Microwave Theory and Techniques, vol. 61, No. 5, May 2013, pp. 2046-2060.
Office Action dated Sep. 2, 2019 in corresponding Taiwan Patent Application No. 108107259.
Office Action dated Mar. 26, 2020 in corresponding Taiwan Patent Application No. 108107258.

VITAL-SIGN DETECTING SYSTEM AND METHOD

CROSS-REFERENCE TO RELATED APPLICATIONS

This application claims priority to Taiwan Patent Applications No. 108107259 and No. 108107258, both filed on Mar. 5, 2019, the entire contents of each of which are herein expressly incorporated by reference.

BACKGROUND OF THE INVENTION

1. Field of the Invention

The present invention generally relates to vital-sign detection, and more particularly to a vital-sign detecting system and method capable of identifying a detected subject.

2. Description of Related Art

Body temperature (BT), blood pressure (BP), heart rate (HR) and respiratory rate (RR) are four primary vital signs. The detection and measurement of the vital signs may be used to evaluate health condition or provide a clue to illness of a person.

Conventional non-contact vital-sign detecting systems are used to remotely monitor vital signs, such as heart rate or respiratory rate, of a detected subject. Due to high cost of the detecting system, it is commonly used to monitor plural detected subjects. However, signals respectively associated with the detected subjects may cause interference and therefore decrease measurement accuracy. Further, it becomes difficult for the detecting system to identify individual detected subjects or may even misidentify the detected subjects when they are close to each other.

A need has thus arisen to propose a novel vital-sign detecting scheme capable of identifying the detected subject to improve the conventional vital-sign detecting systems.

SUMMARY OF THE INVENTION

In view of the foregoing, it is an object of the embodiment of the present invention to provide a vital-sign detecting system and method that can identify a detected subject and enhance accuracy.

According to one embodiment, a vital-sign detecting system includes radio-frequency (RF) tags and at least one RF radar. The RF tags are disposed on detected subjects respectively, the RF tags respectively generate incident RF signals with different predetermined frequencies, and the incident RF signal projects on a corresponding detected subject to generate a corresponding reflected RF signal. The RF radar demodulates the reflected RF signal to obtain vital sign of the corresponding detected subject, and identifies the detected subject according to associated frequency of the reflected RF signal.

DETAILED DESCRIPTION OF THE INVENTION

Figure 1:
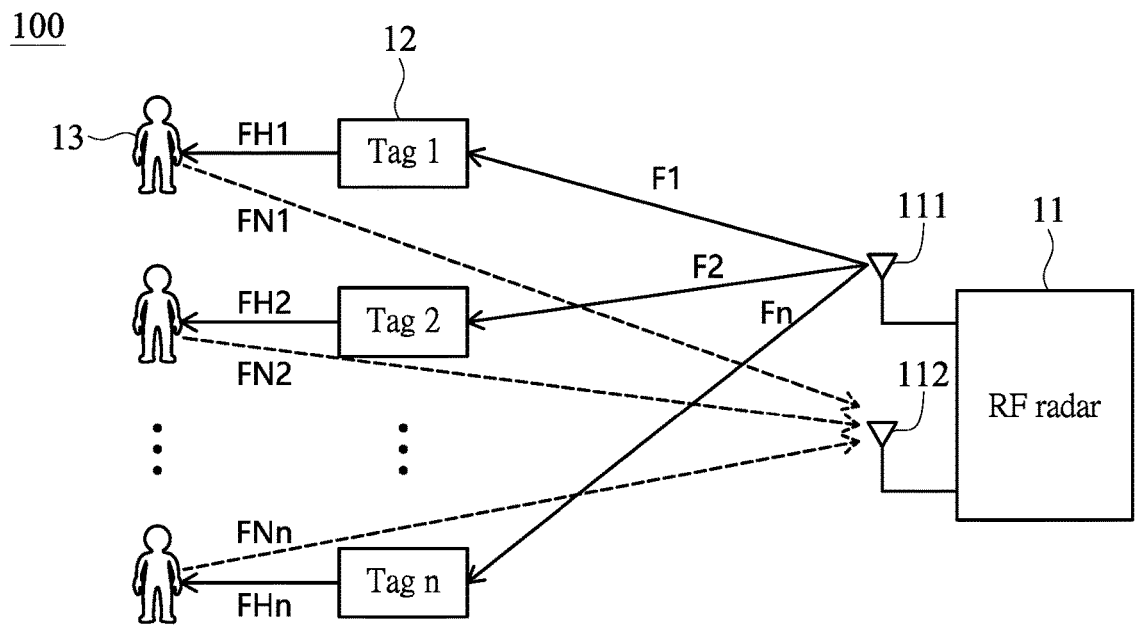
FIG. 1 shows a block diagram illustrating a vital-sign detecting system according to a first embodiment of the present invention.

FIG. 1 shows a block diagram illustrating a vital-sign detecting system 100 (detecting system hereinafter) according to a first embodiment of the present invention. In the embodiment, the detecting system 100 may include a radio-frequency (RF) radar 11 configured to transmit RF signals with predetermined frequencies via a transmitting antenna 111. The detecting system 100 may include harmonic RF tags 12 (tags hereinafter) disposed on (e.g., worn over chest of) detected subjects 13 respectively. The tags 12 may generate incident harmonic (RF) signals respectively according to the RF signals with (different) predetermined frequencies. For example, a tag 1 (12) receives or senses an RF signal F1 transmitted via the transmitting antenna 111, and accordingly generates a corresponding incident harmonic signal FH1 such as second harmonic signal (where FH1 is twice F1 in frequency). The incident harmonic signal FH1 is projected on a detected subject 13 to generate a corresponding reflected harmonic (RF) signal FN1, which may be received by the RF radar 11 via a receiving antenna 112. Body motion of the detected subject 13 modulates the incident harmonic signal and changes phase thereof. Therefore, the RF radar 11 may obtain vital sign, such as respiratory rate or heart rate, of the detected subject 13 by demodulating the reflected harmonic signal. As frequencies of the RF signals received or sensed by the tags 12 are different and frequencies of the incident harmonic signals generated by the tags 12 are different, the RF radar 11 may identify the detected subject 13 corresponding to the received reflected harmonic signal.

Figure 2:
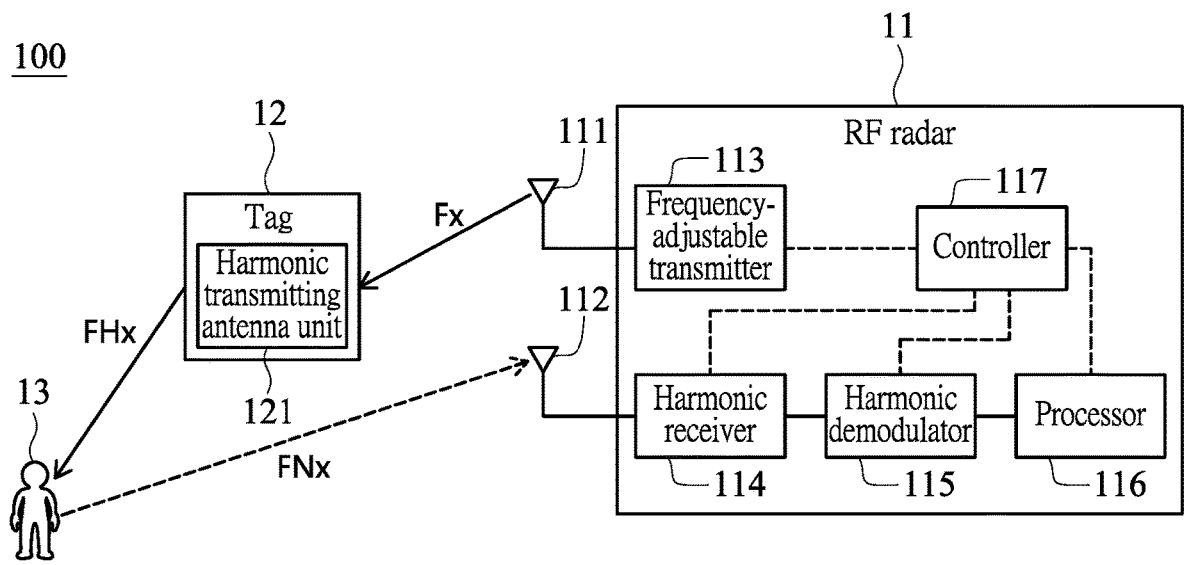
FIG. 2 shows a detailed block diagram of the detecting system of FIG. 1.

FIG. 2 shows a detailed block diagram of the detecting system 100 of FIG. 1. Only one detected subject 13 and the corresponding tag 12 are shown for brevity. In the embodiment, the RF radar 11 may include a frequency-adjustable transmitter 113 configured to generate an RF signal Fx with one of the predetermined frequencies within a predetermined frequency range, for example, by adjusting inductance and/or capacitance of a resonant circuit or an oscillating circuit. The generated RF signal Fx may be transmitted to the tag 12 via the transmitting antenna 111.

The tag 12 of the embodiment may include a harmonic transmitting antenna unit 121 configured to generate resonant reaction when a resonant frequency of the harmonic transmitting antenna unit 121 is the same as the frequency of the RF signal Fx (of the transmitting antenna 111), thereby generating a corresponding incident harmonic signal FHx such as second harmonic signal.

The RF radar 11 of the embodiment may include a harmonic receiver 114 configured to receive a reflected harmonic signal FNx, with frequency being the same as the incident harmonic signal FHx but phase modulated by body motion of the detected subject 13, via the receiving antenna 112.

The RF radar 11 of the embodiment may include a harmonic demodulator 115 configured to demodulate the reflected harmonic signal FNx (received from the harmonic receiver 114) to obtain a baseband signal containing phase change information. The RF radar 11 may include a processor 116 including an analog-to-digital converter and a digital signal processor. The processor 116 is configured to perform analog-to-digital conversion on the baseband signal (outputted from the harmonic demodulator 115) and remove high-frequency component, thereby obtaining vital sign, such as respiratory rate or heart rate, of the detected subject 13 through computation. Specifically, high-frequency component may be removed by the digital signal processor, which may, for example, remove unwanted harmonic signal related to respiration, and remove noise. The RF radar 11 of the embodiment may include a controller 117 configured to control operation of the frequency-adjustable transmitter 113, the harmonic receiver 114, the harmonic demodulator 115 and the processor 116. In the embodiment, as shown in FIG. 2, the frequency-adjustable transmitter 113 is connected to the transmitting antenna 111 to transmit the RF signal Fx, the harmonic receiver 114 is connected to the receiving antenna 112 to receive the reflected harmonic signal FNx, the harmonic demodulator 115 is connected to the harmonic receiver 114 to demodulate the reflected harmonic signal FNx, and the processor 116 is connected to the harmonic demodulator 115 to process the baseband signal.

Figure 3A:
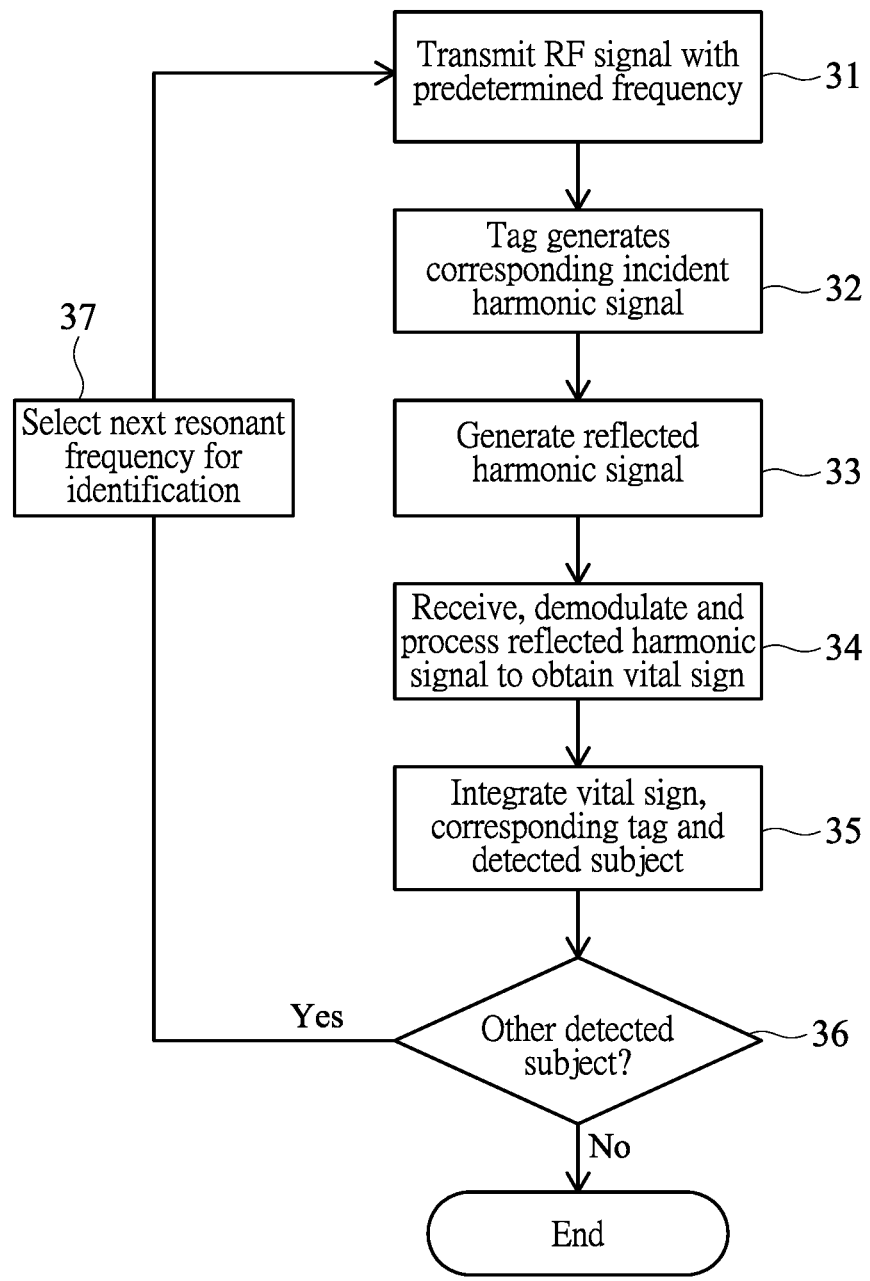
FIG. 3A shows a flow diagram illustrating a vital-sign detecting method according to the first embodiment of the present invention.
Figure 3B:
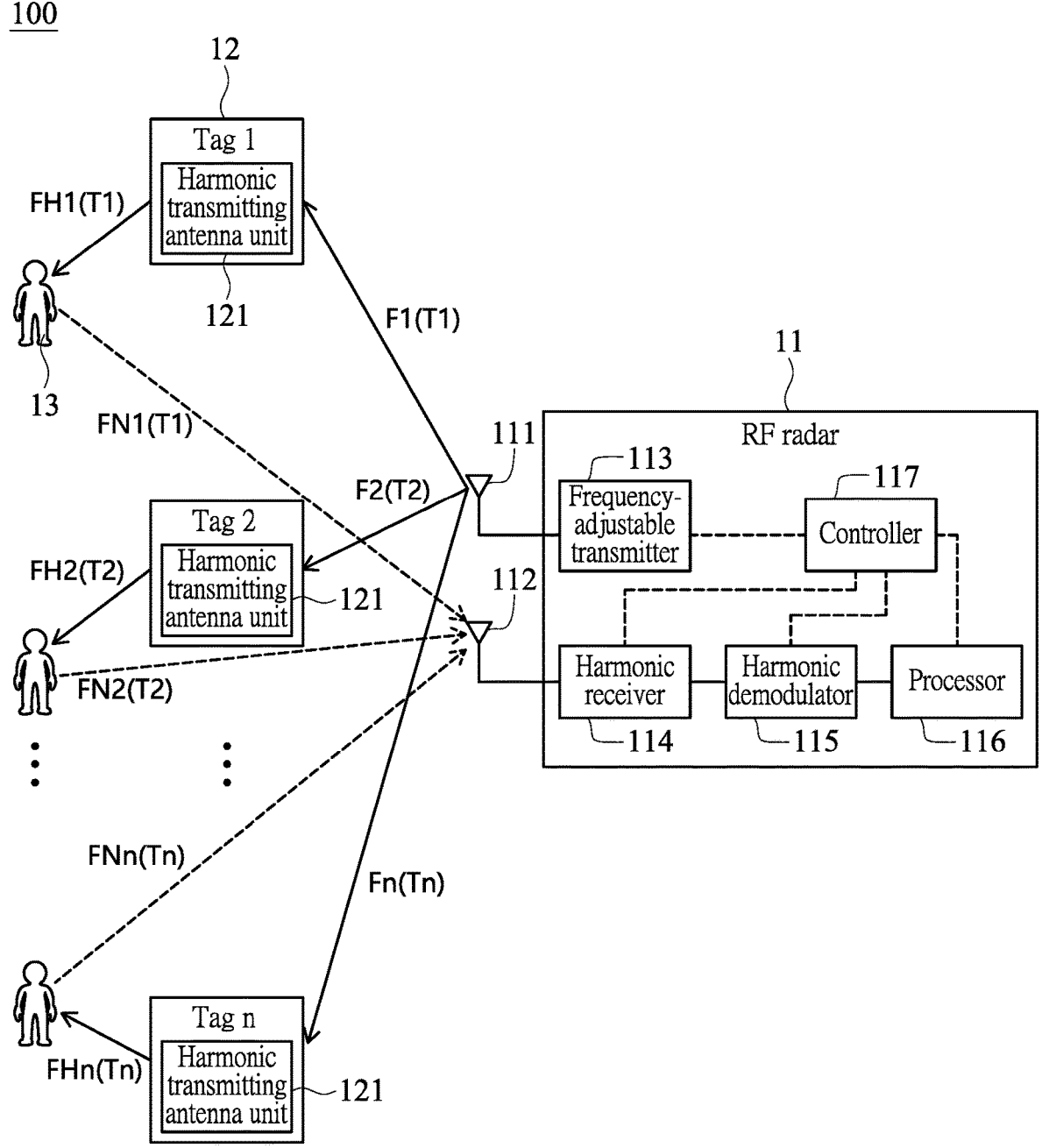
FIG. 3B shows a block diagram illustrating a detecting system associated with FIG. 3A.

FIG. 3A shows a flow diagram illustrating a vital-sign detecting method 300 (detecting method hereinafter) according to the first embodiment of the present invention, and FIG. 3B shows a block diagram illustrating a detecting system 100 associated with FIG. 3A. In step 31, the frequency-adjustable transmitter 113 of the RF radar 11 transmits an RF signal F1 with a predetermined frequency to a tag 1 (12) via the transmitting antenna 111 at time T1. The harmonic transmitting antenna unit 121 of the tag 1 (12) generates resonant reaction with the RF signal F1, thereby generating an incident harmonic signal FH1 to a corresponding detected subject 13 (step 32). It is noted that harmonic transmitting antenna units 121 of other tags 12 would not generate resonant reaction with the RF signal F1, thereby generating no incident harmonic signals FHx to corresponding detected subjects 13.

In step 33, body motion of the detected subject 13 modulates and changes phase of the incident harmonic signal FH1, thereby generating a reflected harmonic signal FN1. In step 34, the harmonic receiver 114 of the RF radar 11 receives the reflected harmonic signal FN1. Subsequently, the harmonic demodulator 115 of the RF radar 11 demodulates the reflected harmonic signal FN1 to obtain a baseband signal containing phase change information. Next, the processor 116 of the RF radar 11 performs analog-to-digital conversion on the baseband signal containing phase change information and removes high-frequency component, thereby obtaining vital sign, such as respiratory rate or heart rate, of the detected subject 13 through computation.

In step 35, the vital sign, the corresponding tag 12 and the detected subject 13 are integrated. The harmonic transmitting antenna unit 121 (of the tag 12) and the RF signal F1 have the same resonant frequency, which can be used as identification (ID) for identifying the detected subject 13.

Next, if there is still detected subject 13 to be detected (step 36), the RF radar 11 selects next resonant frequency for identification (step 37), and steps 31-35 are performed again at time T2. That is, an RF signal F2 with a predetermined frequency is transmitted to a tag 2 (12) at time T2 (step 31), an incident harmonic signal FH2 is generated to a corresponding detected subject 13 (step 32), a reflected harmonic signal FN2 is generated (step 33), vital sign of the detected subject 13 is obtained (step 34), and the vital sign, the corresponding tag 12 and the detected subject 13 are integrated (step 35). If no detected subject 13 is left to be detected in step 36, the flow of the detecting method 300 stops.

Figure 4:
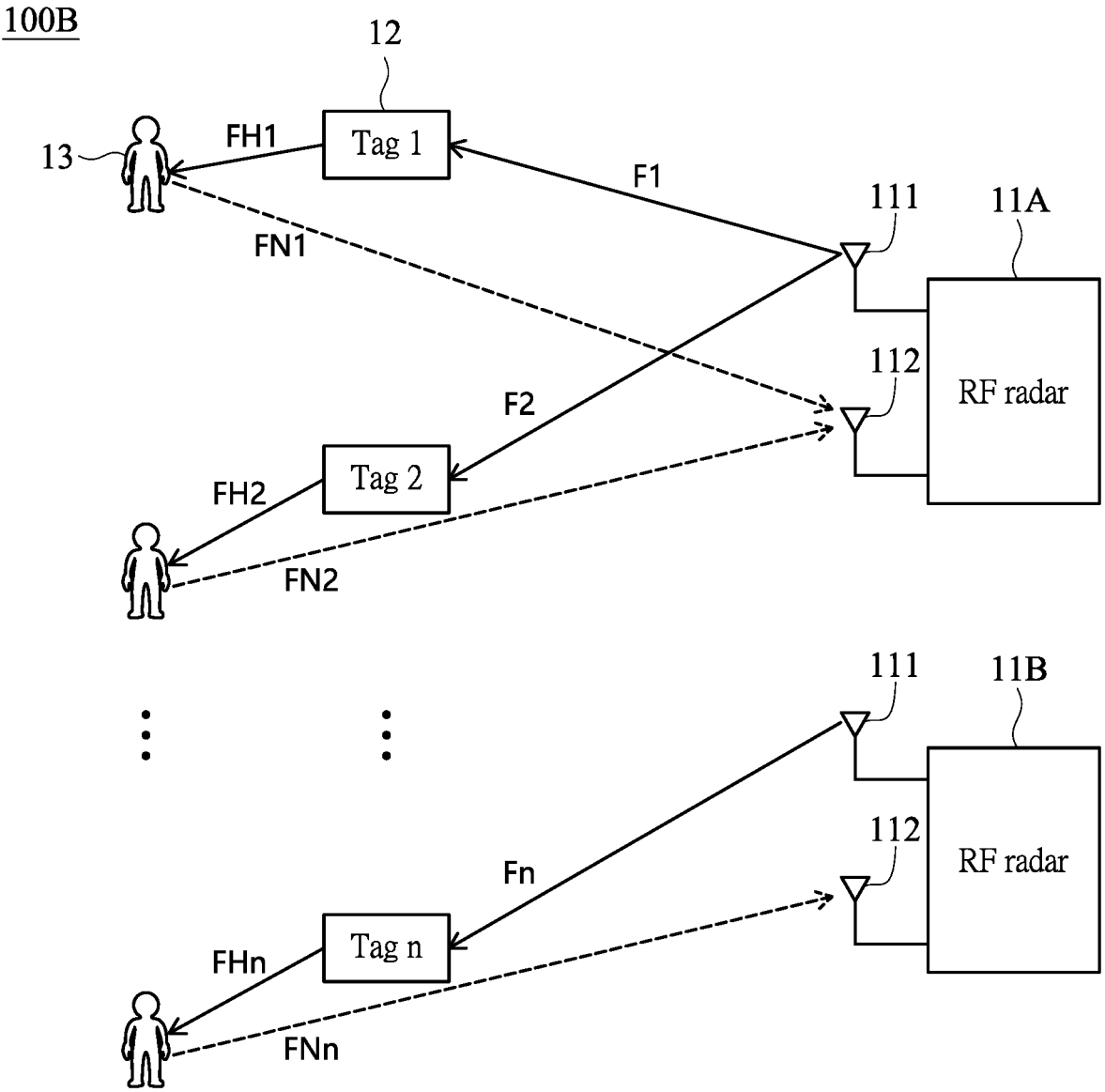
FIG. 4 shows a block diagram illustrating a detecting system according to a first modified embodiment of the first embodiment of the present invention.

FIG. 4 shows a block diagram illustrating a detecting system 100B according to a first modified embodiment of the first embodiment of the present invention. Compared to the detecting system 100 of FIG. 3B, the present embodiment (FIG. 4) adopts plural (e.g., two) RF radars 11A land 11B corresponding to different tags 12 and detected subjects 13 respectively. Accordingly, the RF radars 11A and 11B may perform plural identifications at the same time, while the first embodiment (FIG. 3B) may only perform single identification at a time.

Figure 5:
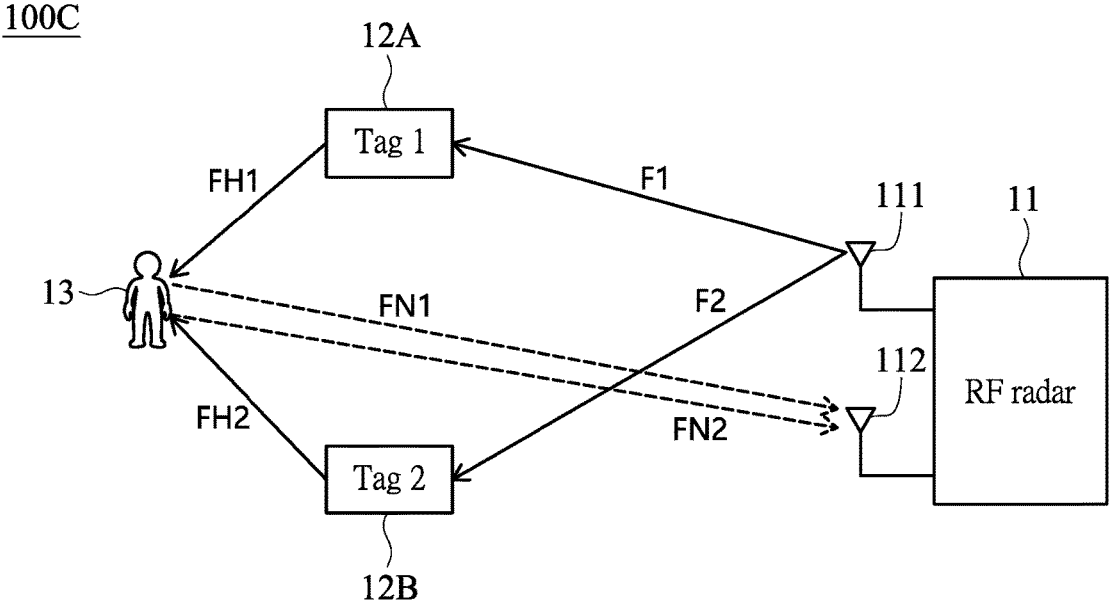
FIG. 5 shows a block diagram illustrating a detecting system according to a second modified embodiment of the first embodiment of the present invention.

FIG. 5 shows a block diagram illustrating a detecting system 100C according to a second modified embodiment of the first embodiment of the present invention. Compared to the detecting system 100 of FIG. 3B, the present embodiment (FIG. 5) adopts more than one of the tags 12 (e.g., tags 12A and 12B) with different resonant frequencies disposed on a single detected subject 13. Accordingly, the RF radar 11 may detect plural vital signs of a single detected subject 13.

Figure 6:
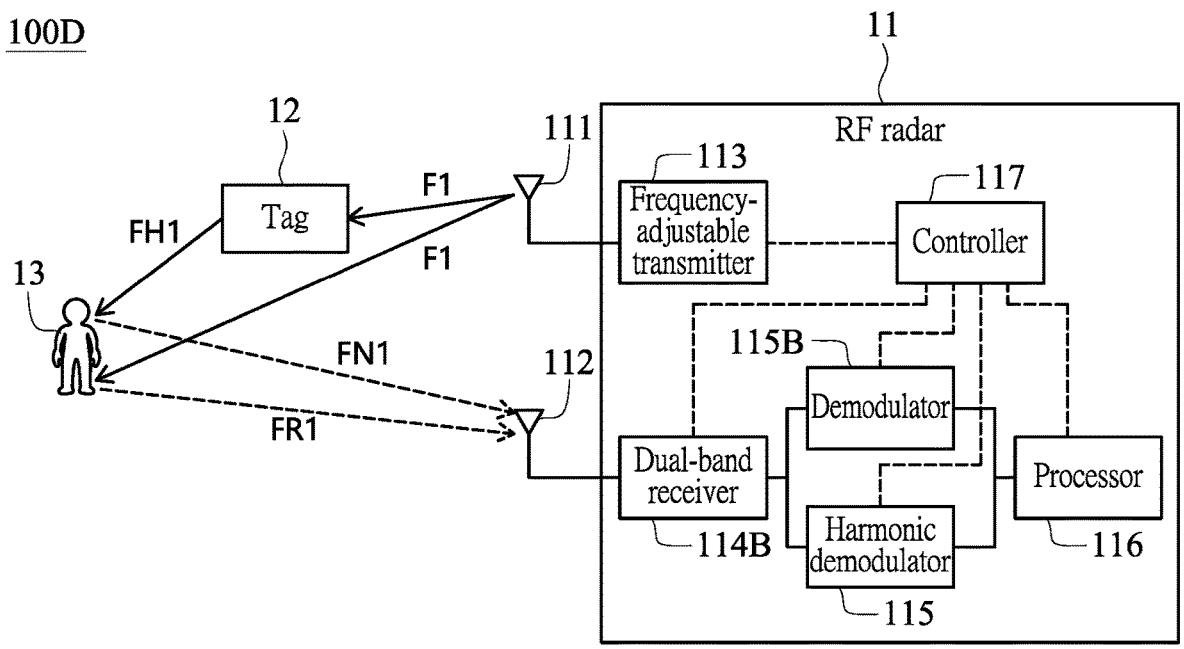
FIG. 6 shows a block diagram illustrating a detecting system according to a third modified embodiment of the first embodiment of the present invention.

FIG. 6 shows a block diagram illustrating a detecting system 100D according to a third modified embodiment of the first embodiment of the present invention. Compared to the detecting system 100 of FIG. 2, the RF radar 11 of the present embodiment (FIG. 6) adopts a dual-band receiver 114B instead of the harmonic receiver 114. One band of the dual-band receiver 114B is similar to that in FIG. 2 for receiving the reflected harmonic signal FN1, and the other band of the dual-band receiver 114B is used to receive a reflected RF signal FR1 reflected from the detected subject 13 (but not via tag 12) who is projected with the RF signal FN1. The received reflected RF signal FR1 is demodulated by a demodulator 115B. Accordingly, the RF radar 11 may detect plural vital signs of a single detected subject 13 by time division multiplexing within the same period.

Figure 7:
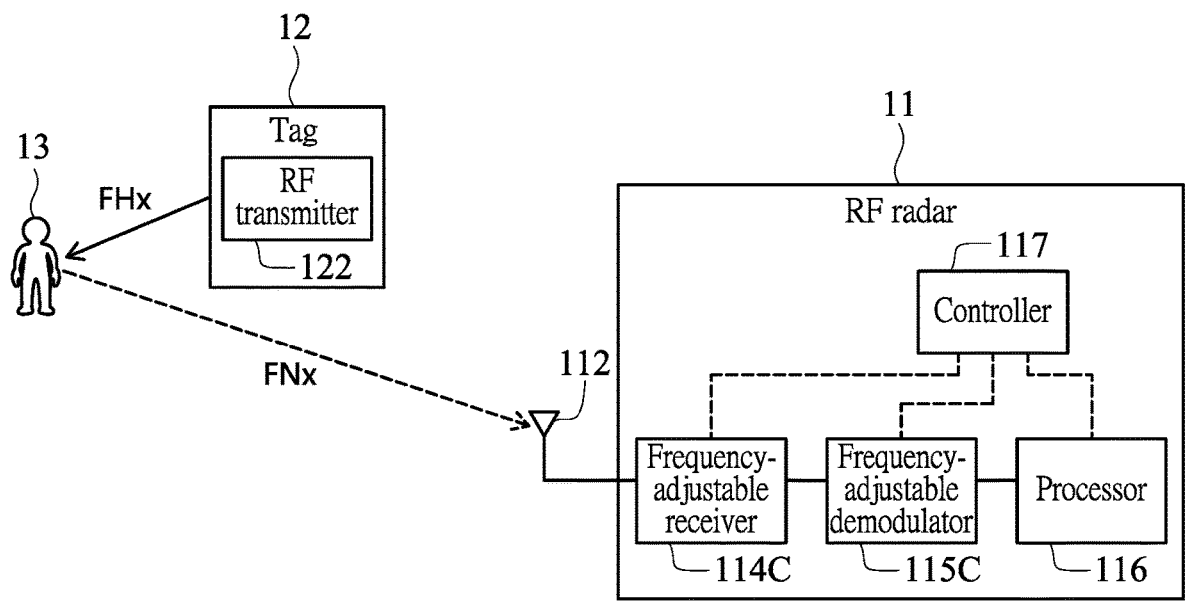
FIG. 7 shows a block diagram illustrating a vital-sign detecting system according to a second embodiment of the present invention.

FIG. 7 shows a block diagram illustrating a vital-sign detecting system 700 (detecting system hereinafter) according to a second embodiment of the present invention. The second embodiment is similar to the first embodiment with the exceptions as described below.

In the embodiment, the RF tag 12 (tag hereinafter) may include an RF transmitter 122 configured to transmit an incident RF signal FHx with a predetermined frequency. Different tags 12 may transmit incident RF signals FHx with different frequencies. The incident RF signal FHx may be projected on the detected subject 13 to generate a corresponding reflected RF signal FNx, which may be received by the receiving antenna 112 of the RF radar 11. Body motion of the detected subject 13 may modulate the incident RF signal FHx and change phase thereof, and generate the corresponding reflected RF signal FNx. Therefore, the RF radar 11 may obtain vital sign, such as respiratory rate or heart rate, of the detected subject 13 by demodulating the reflected RF signal.

The RF radar 11 of the embodiment may include a frequency-adjustable receiver 114C (instead of the harmonic receiver 114 as in the first embodiment) configured to receive the reflected RF signals FNx within a predetermined frequency range. The RF radar 11 of the embodiment does not require the frequency-adjustable transmitter 113 and the transmitting antenna 111 as in the first embodiment. The RF radar 11 of the embodiment may include a frequency-adjustable demodulator 115C configured to demodulate the received reflected RF signal FNx within a predetermined frequency range.

Figure 8A:
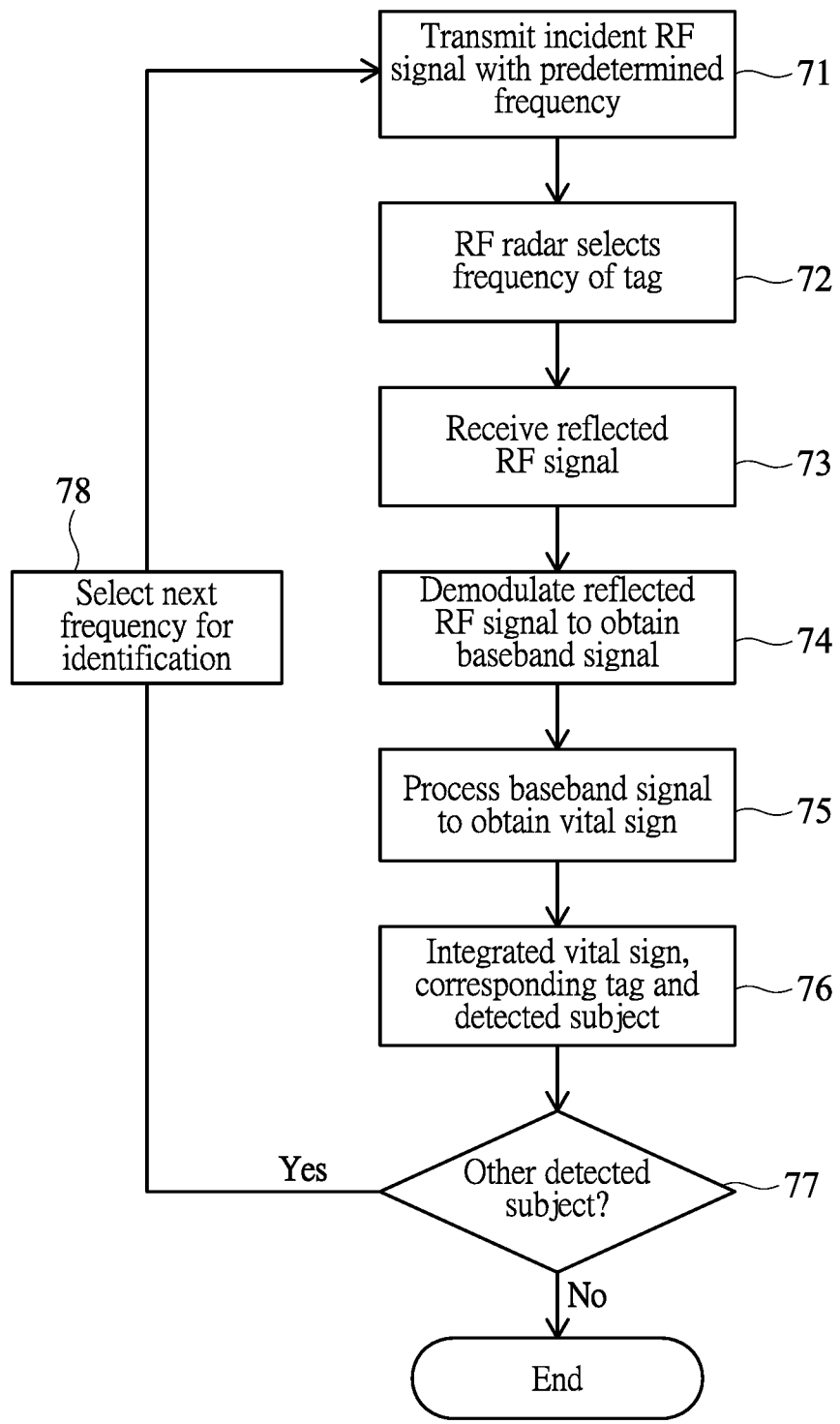
FIG. 8A shows a flow diagram illustrating a vital-sign detecting method according to the second embodiment of the present invention.
Figure 8B:
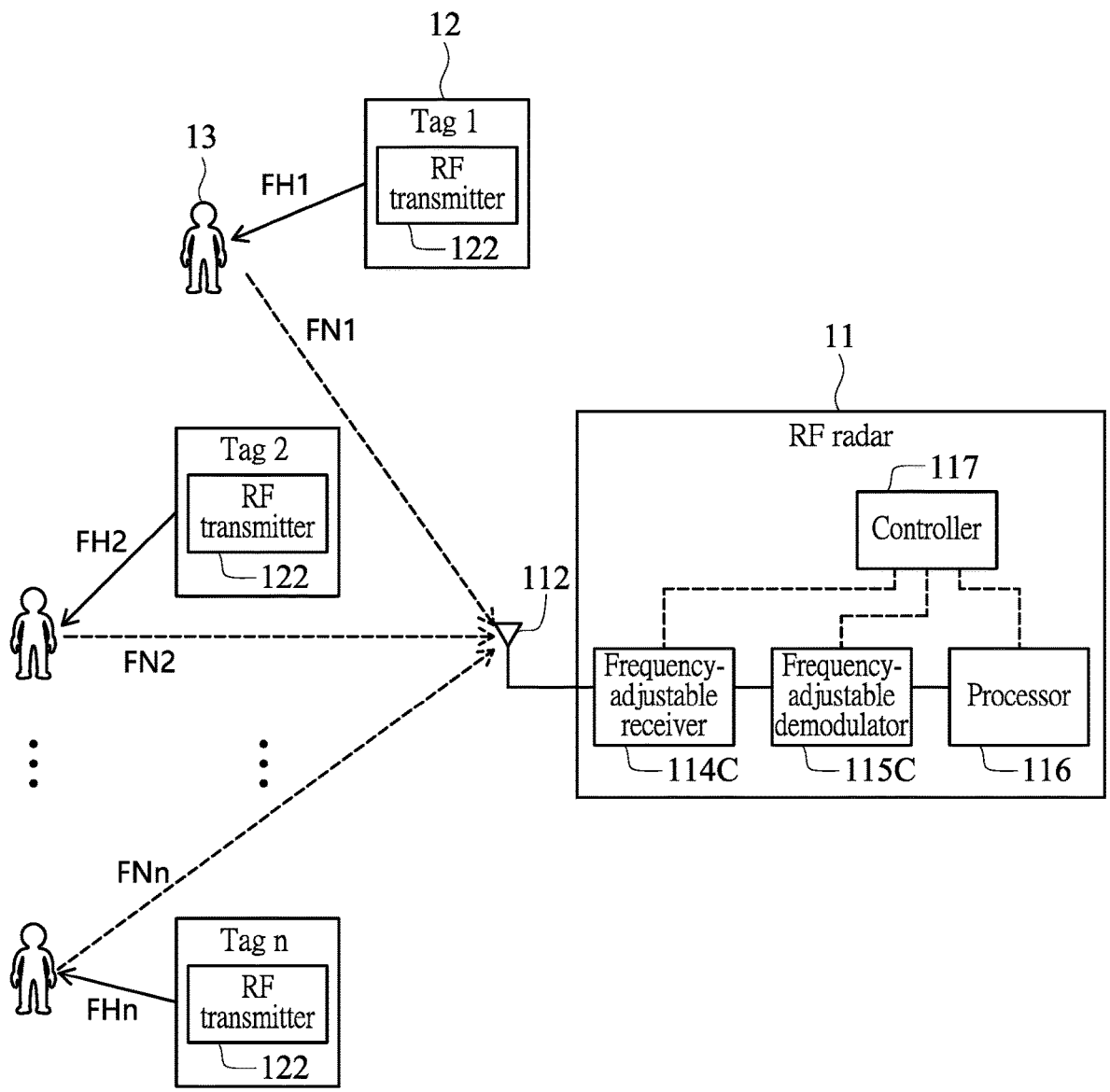
FIG. 8B shows a block diagram illustrating a detecting system associated with FIG. 8A.

FIG. 8A shows a flow diagram illustrating a vital-sign detecting method 800 (detecting method hereinafter) according to the second embodiment of the present invention, and FIG. 8B shows a block diagram illustrating a detecting system 700 associated with FIG. 8A. In step 71, the tags 12 transmit incident RF signals FHx (x is from 1 to n) with (different) predetermined frequencies to respective detected subjects 13. In step 72, the RF radar 11 selects a frequency of one of the tags 12. Body motion of the detected subject 13 modulates the incident RF signal FHx and changes phase thereof, thereby generating a reflected RF signal FNx (x is from 1 to n).

In step 73, the frequency-adjustable receiver 114C of the RF radar 11 receives the reflected RF signal FNx. Next, in step 74, the frequency-adjustable demodulator 115C of the RF radar 11 demodulates the reflected RF signal FNx to obtain a baseband signal containing phase change information. In step 75, the processor 116 of the RF radar 11 performs analog-to-digital conversion on the baseband signal containing phase change information and removes high-frequency component, thereby obtaining vital sign, such as respiratory rate or heart rate, of the detected subject 13 through computation.

In step 76, the vital sign, the corresponding tag 12 and the detected subject 13 are integrated. The RF transmitter 122 (of the tag 12) and the frequency-adjustable receiver 114C (of the RF radar 11) have the same frequency, which can be used as identification (ID) for identifying the detected subject 13.

Next, if there is still detected subject 13 to be detected (step 77), (the frequency-adjustable receiver 114C of) the RF radar 11 selects next frequency for identification (step 78), and steps 71-76 are performed again. If no detected subject 13 is left to be detected in step 77, the flow of the detecting method 800 stops.

Figure 9:
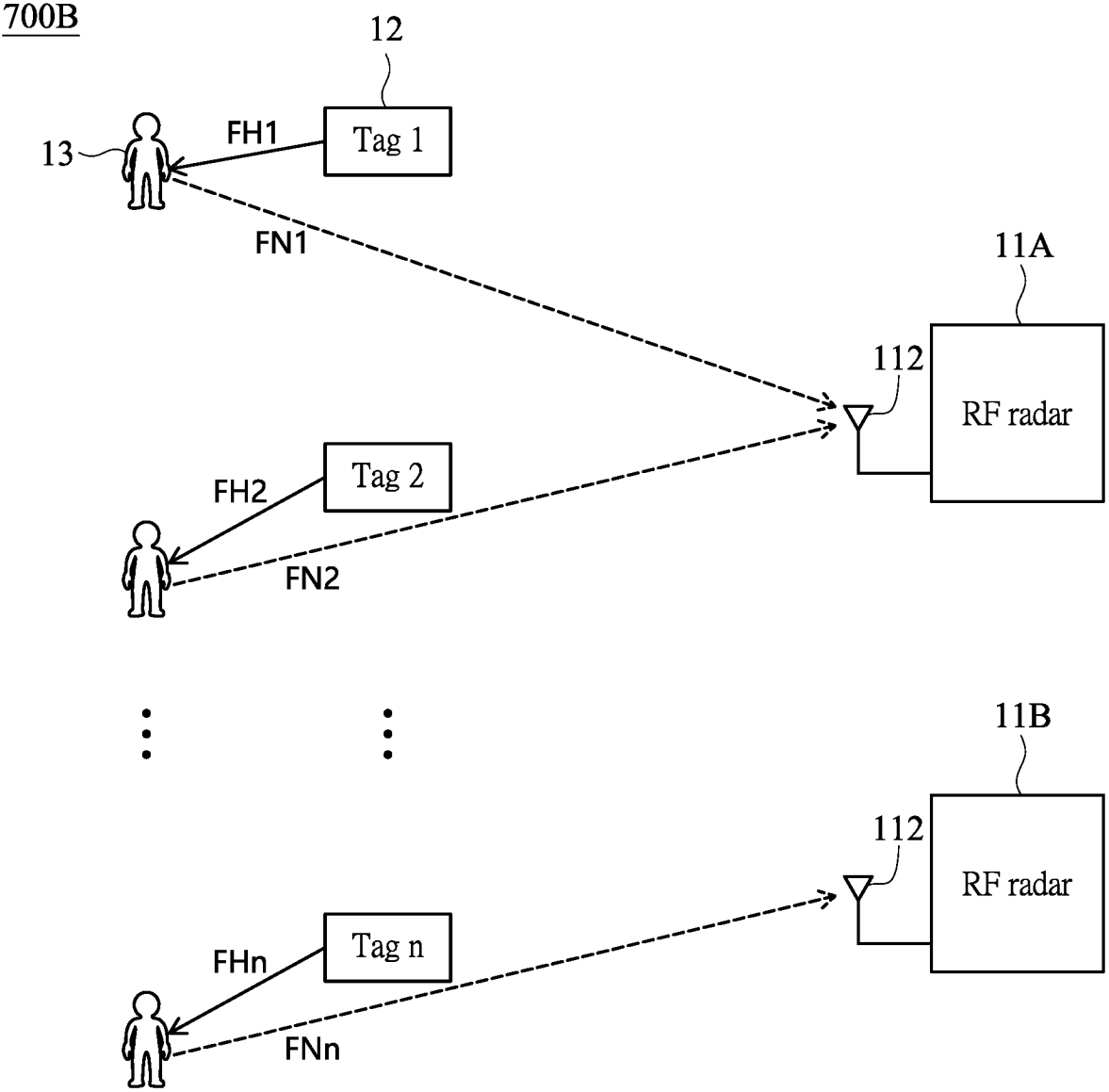
FIG. 9 shows a block diagram illustrating a detecting system according to a first modified embodiment of the second embodiment of the present invention.

FIG. 9 shows a block diagram illustrating a detecting system 700B according to a first modified embodiment of the second embodiment of the present invention. Compared to the detecting system 700 of FIG. 8B, the present embodiment (FIG. 9) adopts plural (e.g., two) RF radars 11A land 11B corresponding to different tags 12 and detected subjects 13 respectively. Accordingly, the RF radars 11A and 11B may perform plural identifications at the same time, while the second embodiment (FIG. 8B) may only perform single identification at a time.

Figure 10:
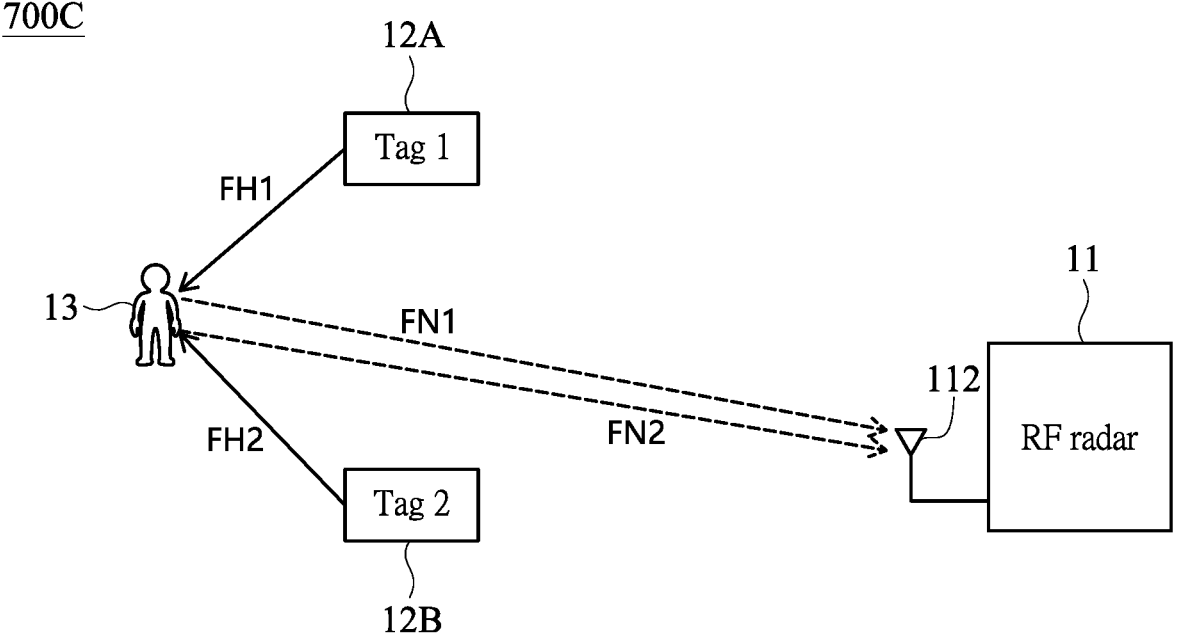
FIG. 10 shows a block diagram illustrating a detecting system according to a second modified embodiment of the second embodiment of the present invention.

FIG. 10 shows a block diagram illustrating a detecting system 700C according to a second modified embodiment of the second embodiment of the present invention. Compared to the detecting system 700 of FIG. 7, the present embodiment (FIG. 10) adopts more than one of the tags 12 (e.g., tags 12A and 12B) with different frequencies disposed on a single detected subject 13. Accordingly, the RF radar 11 may detect plural vital signs of a single detected subject 13.

Although specific embodiments have been illustrated and described, it will be appreciated by those skilled in the art that various modifications may be made without departing from the scope of the present invention, which is intended to be limited solely by the appended claims.

What is claimed is:

1. A vital-sign detecting system, comprising:
a plurality of radio-frequency (RF) tags disposed on detected subjects respectively, the RF tags respectively generating incident RF signals with different predetermined frequencies, and the incident RF signal projecting on a corresponding detected subject to generate a corresponding reflected RF signal; and
at least one RF radar that demodulates the reflected RF signal to obtain vital sign of the corresponding detected subject, and identifies the detected subject according to associated frequency of the reflected RF signal;
wherein the RF tags generate the incident RF signals independent of the RF radar, and frequencies of the incident RF signals are different.

2. The system of claim 1, wherein the RF radar comprises:
a frequency-adjustable receiver that receives the reflected RF signal with one of the predetermined frequencies within a predetermined frequency range; and
a frequency-adjustable demodulator that demodulates the reflected RF signal to obtain a baseband signal.

3. The system of claim 2, wherein the RF radar further comprises:
a processor that performs analog-to-digital conversion on the baseband signal and remove high-frequency component thereof, thereby obtaining vital sign of the detected subject through computation.

4. The system of claim 1, wherein said at least one RF radar comprises a plurality of RF radars for demodulating the reflected RF signals with predetermined frequencies respectively.

5. The system of claim 1, wherein more than one of the RF tags are disposed on at least one of the detected subjects.

6. A vital-sign detecting method, comprising:
generating an incident RF signal with one of different predetermined frequencies;
projecting the incident RF signal on a corresponding detected subject to generate a corresponding reflected RF signal;
demodulating the reflected RF signal to obtain vital sign of the corresponding detected subject; and
identifying the detected subject according to associated frequency of the reflected RF signal;
wherein the RF tags generate the incident RF signals independent of the RF radar, and frequencies of the incident RF signals are different.

7. The method of claim 6, wherein the reflected RF signal is demodulated to obtain a baseband signal.

8. The method of claim 7, further comprising:
performing analog-to-digital conversion on the baseband signal and removing high-frequency component thereof, thereby obtaining vital sign of the detected subject through computation.

* * * * *